(12) United States Patent
Eidenberger

(10) Patent No.: US 8,569,247 B2
(45) Date of Patent: Oct. 29, 2013

(54) HYDROLYSATE OF CROCIN

(75) Inventor: Thomas Eidenberger, Steyr (AT)

(73) Assignee: Omnica GmbH, Hamburg (DE)

( * ) Notice: Subject to any disclaimer, the term of this patent is extended or adjusted under 35 U.S.C. 154(b) by 114 days.

(21) Appl. No.: 12/706,959

(22) Filed: Feb. 17, 2010

(65) Prior Publication Data

US 2010/0210572 A1    Aug. 19, 2010

Related U.S. Application Data

(60) Provisional application No. 61/153,357, filed on Feb. 18, 2009.

(51) Int. Cl.
*A61K 31/70* (2006.01)
*C07H 11/00* (2006.01)
*C07H 15/00* (2006.01)

(52) U.S. Cl.
USPC .................. 514/25; 514/53; 536/4.1; 536/115

(58) Field of Classification Search
None
See application file for complete search history.

(56) References Cited

FOREIGN PATENT DOCUMENTS

| CN | 10 1 225 040 | 7/2008 |
| ES | 2 238 004 | 8/2005 |
| JP | 07 018194 | 1/1995 |
| WO | WO 2004/078695 | 9/2004 |

OTHER PUBLICATIONS

Pfister S. et al., "Isolation and Structure Elucidation of Carotenoid-glycosyl esters in Gardenia Fruits (*Gardenia jasminoides* Ellis) and saffron (*Crocus sativus* Linne)", Journal of Agricultural and Food Chemistry, vol. 44, No. 9, 1996, pp. 2612-2615, XP002581298.
Zhang H. et al., "Semi-preparative isolation of crocins from saffron (*Crocus sativus* L.)", Chromatographia 200406 DE, vol. 59, No. 11-12, Jun. 2004, pp. 691-696, XP002581299.
Dufresne Christiane et al., "In vitro formation of crocetin glucosyl esters by *Crocus sativus* callus extract", Planta Medica, vol. 63, No. 2, 1997, pp. 150-151, XP9133076.
Asai Akira et al., "Orally administered crocetin and crocins are absorbed into blood plasma as croetin and its glucuronide conjugates in mice", Journal of Agricultural and Food Chemistry, vol. 53, No. 18, Sep. 2005, pp. 7302-7306, XP002581301.
Xi et al., "Pharmacokinetic properties of crocin (crocetin digentiobiose ester) following oral administration in rats", Phytomedicine, Gustav Fischer Verlag, Stuttgart Lnkd DOI:10.1016/J.Phymed.2006.11.028, pp. 633-636, XP022183747.
Soeda S. et al., "Pharmacological activities of crocin in saffron", Journal of Natural Medicines 200704 JP Lnkd- DOI:10.1007/S11418-006-0120-9, vol. 61, No. 2, Apr. 2007, pp. 102-111, XP002581302.
In-Ah Lee et al., "Antihyperlipidemic Effect of Crocin Isolated from the Fructus of *Gardenia jasminoides* and Its Metabolite Crocetin", Biological & Pharmaceutical Bulletin 28(11), pp. 2106-2110, 2005.
International Search Report PCT/EP2010/052064 dated May 28, 2010 (5 pgs.).
Carmona, et al., "A New Approach to Saffron Aroma", Critical Reviews in Food Science and Nutrition, No. 47, 2007, pp. 145-159.
Carmona, et al., "Crocetin Esters, Picrocrocin and Its Related Compounds Present in *Crocus sativus* Stigmas and *Gardenia jasminoides* Fruits. Tentative Identification of Seven New Compounds by LC-ESI-MS", Agric. Food Chem., No. 54, 2006, pp. 973-979.
Carmona, et al., "Influence of Different Drying and Aging Conditions on Saffron Constituents", J. Agric. Food Chem. No. 53, 2005, pp. 3974-3979.
Iborra, et al., "TLC Preparative Purification of Picrocrocin, HTCC and Crocin from Saffron", Journal of Food Science—vol. 57, No. 3, 1992, pp. 714-731.
Park, et al., "Quantitative Analysis of Crocetin Colorants in Gardenias (*Gardenia jasminoides* Ellis) by LC/DAD/MS", J. Ind. Eng. Chem. vol. 7, No. 6, 2001, pp. 375-379.
Morimoto, et al., "Post-Harvest Degradation of Carotenoid Glucose Esters in Saffron", Planta Med. 60, 1994, pp. 438-440.
Tarantilis, et al., "Determination of saffron (*Crocus sativus* L.) components in crude plant extract using highperformance liquid chromatography-UV-visible photodiode-array detection-mass spectrometry" Jou. of Chromatography A, No. 699, 1995, pp. 107-118.

*Primary Examiner* — Elli Peselev
(74) *Attorney, Agent, or Firm* — Fulbright & Jaworski, L.L.P.; Scott D. Rothenberger; Colin L. Fairman

(57) ABSTRACT

The present invention relates to a composition derived from the hydrolysate of plant containing crocin or the derivatives thereof. The composition includes a significant amount of crocetin monoester. The present invention also provides a method to hydrolyze crocin existing in a plant extract, and further relates to the use.

14 Claims, 6 Drawing Sheets

HYDROLYSATE OF CROCIN

CROSS REFERENCE TO RELATED APPLICATIONS

This application claims benefit of U.S. Ser. No. 61/153,357, filed on Feb. 18, 2009, entitled "HYDROLYSATE OF CROCIN" by Thomas Eidenberger, the contents of which are incorporated in their entirety herein by reference.

FIELD OF THE INVENTION

The present invention relates to a composition comprising an increased amount of crocetin monoester relative to a naturally occurring amount, which is derived from the hydrolysate of a plant material containing crocin or derivatives thereof. The present invention also provides a method to hydrolyze crocin existing in a plant extract, and further relates to its use.

BACKGROUND OF THE INVENTION

As a bright yellow color, crocin/crocetin has been in use for over a thousand years. Usually the colorants are extracted from dried saffron stigma or from the dried fruits of gardenia.

Saffron is obtained by drying the stigmas from the flower of *Crocus sativus* L., whose cultivation probably began during prehistoric Greek times. About 200 stigmas are required to obtain 1 g of colorant. The basic components of saffron, which are responsible for its strong yellow-red color, are cis- and trans-crocins, a family of water-soluble carotenoids.

Saffron (*Crocus sativus*) is not a vegetable, although in some areas of the world the corms of various crocus species are eaten by local peasants. Saffron is one of the most expensive spices on the earth, which has a pleasant spicy, pungent, bitter taste and a tenacious odor. Fortunately, small quantities of saffron go a long way in terms of flavoring. Besides being steeped in tea, it is used for seasoning many foods such as fancy rolls, biscuits, rice, and fish. The slender dried flower stigmas of the saffron constitute the true saffron of commerce. Both of the wholesale price and the retail price are expensive in the marketplace, but saffron has always been popular as a yellowish orange natural dyestuff.

Gardenia (*Gardenia jasminoides*) is another prevailing plant being used for yellow dye. Gardenia has also been used in Japan and China as herbal drugs for their antiphlogistic, diuretic, antipyretic, haemostatic, and cholagogic effects, and can be used to treat contusions. A paste of the herb with flour and wine is used as a poultice on twists, sprains, strains, bruises, and abscesses; very effective in injuries to tendons, ligaments, joints and muscles. Furthermore, it is an important crude drug in traditional Asian medical prescriptions, which have sedative, antipyretic, diuretic, choleretic, and anti-inflammatory effects. Gardenia yellow has been listed in The Japanese Pharmacopoeia as crude drug. In Chinese medicine, it is considered to have anti-inflammatory, antipyretic, astringent, and haemostatic functions as well as use in the treatment of mastitis. It is also used for irritation, sore and swollen eyes and abscesses.

Gardenia yellow is a yellowish food colorant and a member of the carotenoid family. Its principal pigments are crocin/crocetin derivatives. Gardenia yellow is obtained by extraction with water or ethanol from the fruit of Gardenia. The main component of gardenia yellow is crocin, which is now generally used as a natural yellow pigment. It is very soluble in water compared to other carotenoids. Gardenia yellow is listed in the list of existing food additives in Japan. For example, gardenia yellow pigment has been used as food colorant for Japanese traditional foods, such as ohan (yellow rice colored with gardenia fruit) and kuri-kanroni (yellow chestnuts colored with gardenia fruit and soaked in syrup).

Crocetin is a natural carotenoid dicarboxylic acid (8,8'-Diapo-$\psi$,$\psi$-carotenedioic acid), which is a brick red crystal with a melting point of 285° C. Chemically, crocetin is a polyene di-carboxylic acid (8,8'-diapocarotene-8,8'-diolic acid), whose central unit consists of seven conjugated double bonds and four chain methyl groups. When one or both of the end-groups (carboxyl groups) of crocetin are esterified with glucose or gentiobiose, di-esters of crocetin are produced which can have two equal or different end-groups.

In one aspect, crocin is bis(6-O-$\beta$-D-glucopyranosyl-$\beta$-D-glucopyranosyl)ester, $\alpha$-crocin, or di-gentiobiose ester of crocetin, having a chemical structure as shown below:

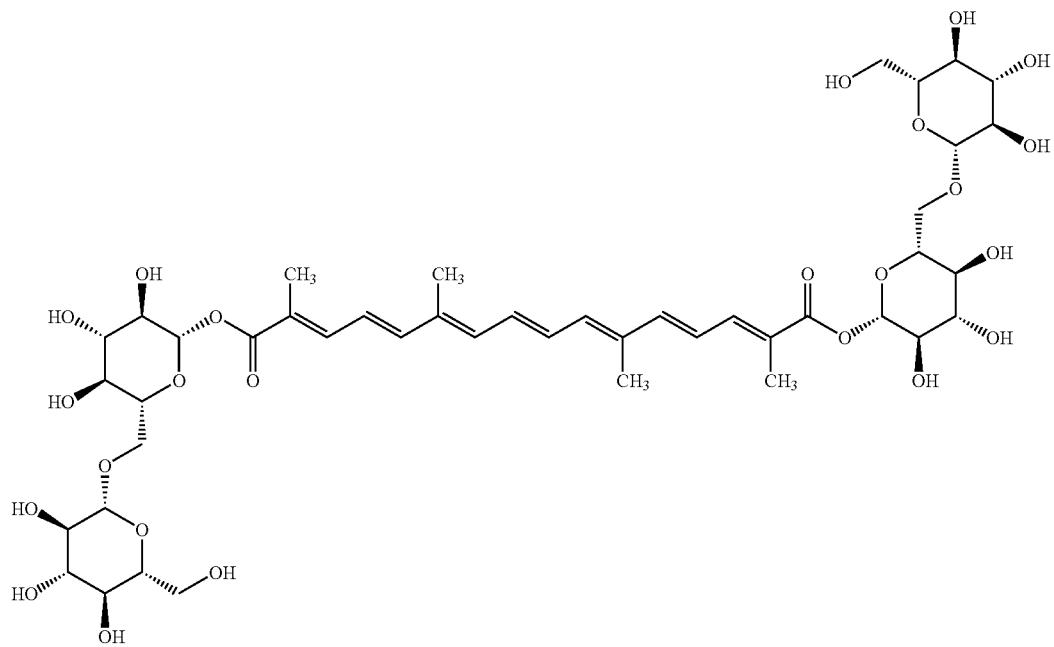 [SMILES: CC(/C=C/C=C(\C)C(=O)O[C@@H]1O[C@H](CO[C@@H]2O[C@H](CO)[C@@H](O)[C@H](O)[C@H]2O)[C@@H](O)[C@H](O)[C@H]1O)=C\C=C\C=C(C)\C=C\C=C(/C)C(=O)O[C@@H]1O[C@H](CO[C@@H]2O[C@H](CO)[C@@H](O)[C@H](O)[C@H]2O)[C@@H](O)[C@H](O)[C@H]1O]

In a broader sense, crocin also includes natural carotenoids where the sugar moiety is not limited to digentiobiose, and can be defined as a diester formed as the condensation product of any saccharide and the dicarboxylic acid crocetin. This is shown below:

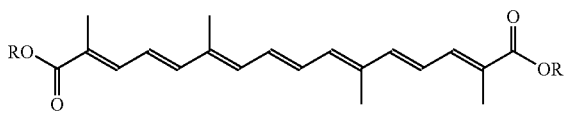

wherein R is any sugar residue and each R, independently, can be the same or different.

The chemical structure of crocetin is shown as below,

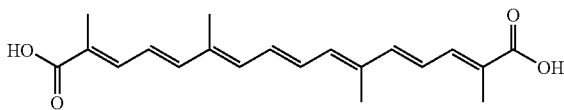 [SMILES: CC(/C=C/C=C(\C)C(=O)O)=C\C=C\C=C(C)\C=C\C=C(/C)C(=O)O]

which is the central core of crocin, and is also the compound responsible for the color of saffron. Crocetin is commercially obtained by hydrolyzing crocin to remove digentiobiose of crocin.

Crocin has been shown to be a potent antioxidant, as well as being useful for anti-depression, cancer prevention, enhancing mental function, lowering high cholesterol, and/or inflammation prevention. Crocin, crocetin and its derivatives have also been shown to be able to stimulate bile secretion significantly, being useful to improve many conditions. In China, a saffron multi-glycoside tablet has been approved as a novel oral drug for the treatment of coronary heart disease and angina. This drug product consists of a series of components extracted from saffron, among which crocin is established as the main effective ingredient and the standard control.

Crocin is a unique water-soluble carotenoid, which has attracted much research attention for its extensive pharmacological effects. Current research provides that crocin has a big molecular structure that is unsuitable to be absorbed in vivo. It was also found that crocin was not absorbed after oral administration to animals and healthy volunteers (*Phytomedicine* 14 (2007) 633-36).

Crocetin is recognized as one of the active metabolites of crocin in the body, but the increase of crocetin was not significant after repeated oral dose, which indicates that crocetin was rapidly eliminated without accumulation in the body. One possible reason might be that crocetin is insoluble in water. Low solubility in water limits many practical applications in food, beverage, drug or nutraceuticals, which also result in reduced bioavailability in vivo.

The investigations on the biological and pharmacological activities of crocin/crocetin were obtained from the experiments in vitro or on animals, but few studies have taken into account the bioavailability of crocin/crocetin and their derivatives.

Therefore, a need exits for suitable crocin/crocetin derivatives that have increased bioavailability relative to crocin or crocetin.

BRIEF SUMMARY OF THE INVENTION

In one aspect, the present invention surprisingly provides compositions derived from the hydrolysate of a plant material containing crocin or derivatives thereof. The hydrolysates include an increased amount of a crocetin monoester relative to lack of naturally occurring crocetin monoesters found in crocin materials, including extracts. For example, crocetin monoester is crocetin mono glucosyl ester, crocetin mono gentiobiosyl ester or mixtures thereof.

Generally, the compositions have an increased content of crocetin monoester by more than 1% by weight relative to the amount of monoester that occurs naturally in a plant material that includes crocins. Since crocetin monoesters do not occur in the natural state, there is an increased amount of monoesters in the present hydrolysates.

In one aspect, the hydrolysate compositions of the invention can include crocin, crocetin, or other crocetin monoesters wherein the ratio of crocin:monoester:crocetin is from about (0-25):(1-80):(1-60) by weight, or wherein the ratio of crocin: monoester:crocetin is from about (5-15):(10-60):(5-50) by weight, or wherein the ratio of crocin:monoester:crocetin is from about (10-15):(30-50):(30-40) by weight, or even wherein the ratio of crocin:monoester:crocetin is from about 10 to about 40 to about 40 by weight.

Generally, the plant containing crocin is gardenia or saffron.

The present invention also provides a method to prepare the hydrolysate compositions described herein, wherein the hydrolysate is from the hydrolysis under acidic or basic conditions. For example, acidic hydrolysis utilizes HCl, phosphoric acid or oxalic acid.

The hydrolysates described herein can be used in the comestic, pharmaceutical, nutraceutical or as a dietary supplement.

The hydrolysates described herein can be used for treating, preventing or improving depression, cancer, gynecological inflammation, atherosclerosis, cardiovascular diseases, Alzheimer's disease, aged-related macular degeneration, hepatitis, cirrhosis, liver cancer lowering high cholesterol, adjusting bile secretion, or enhancing brain health.

DETAILED DESCRIPTION

Figure 1:
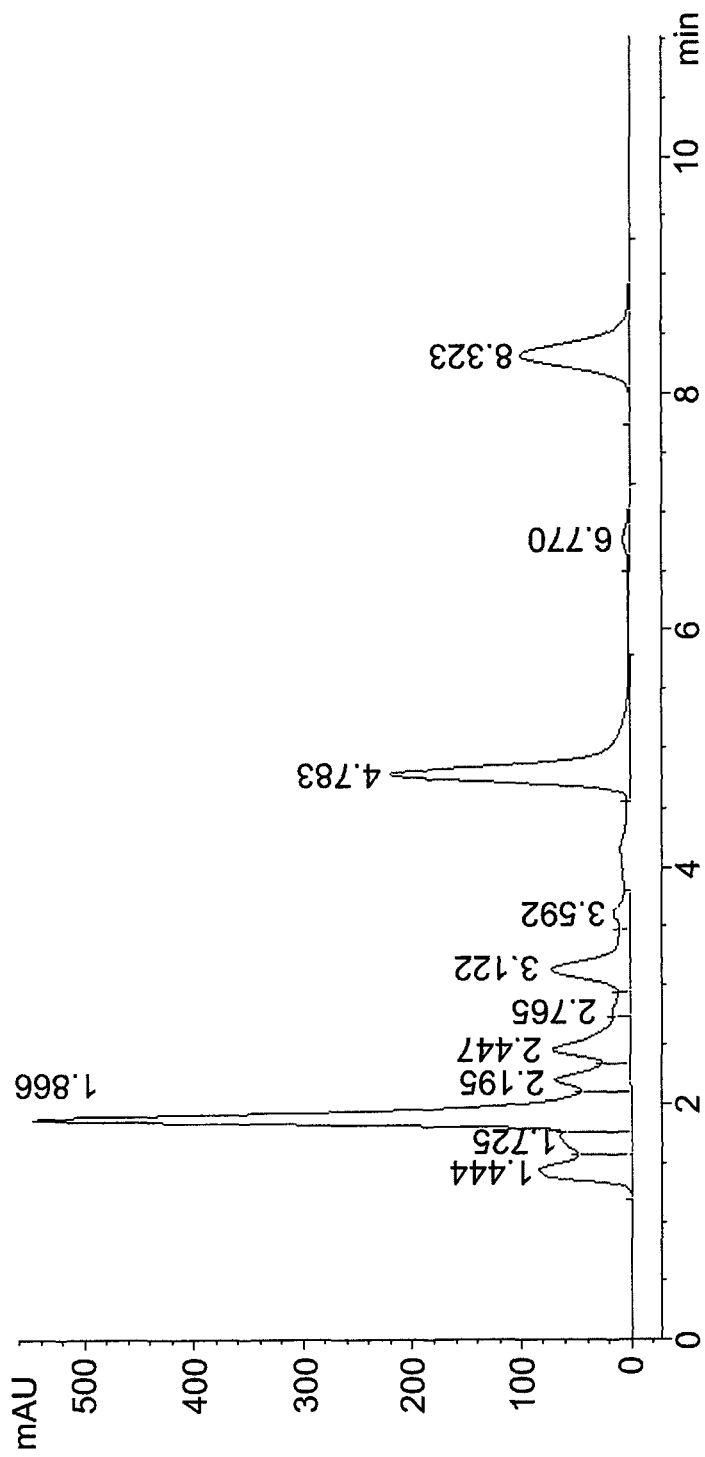
FIG. 1 is an HPLC chromatogram of a hydrolysate of one embodiment of the invention.
Figure 2:
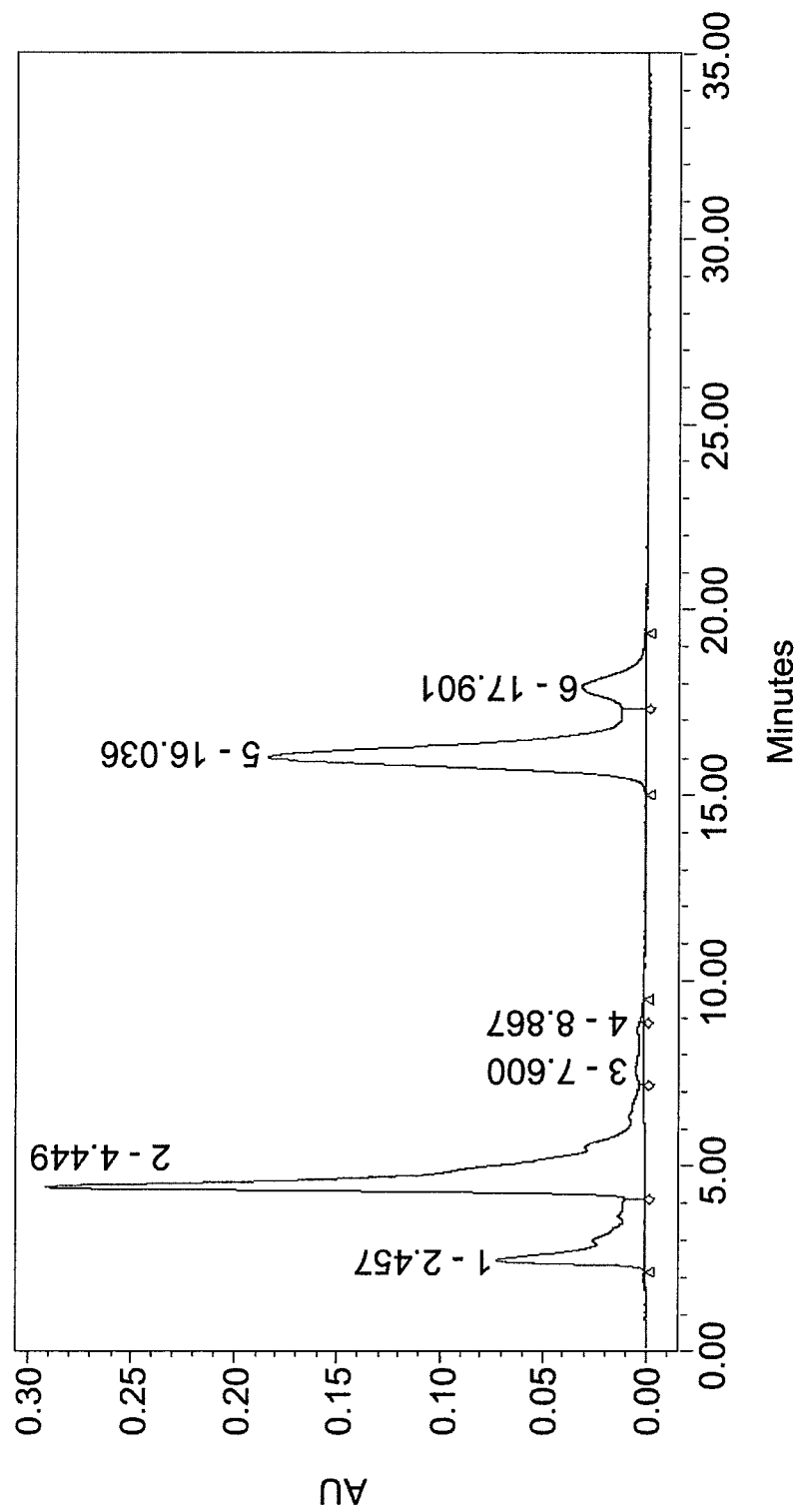
FIG. 2 is an HPLC chromatogram of a hydrolysate of another embodiment of the invention.

In the specification and in the claims, the terms "including" and "comprising" are open-ended terms and should be interpreted to mean "including, but not limited to. . . . " These terms encompass the more restrictive terms "consisting essentially of" and "consisting of:"

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention is directed to a composition comprising a monoester of crocetin, which is derived from the hydrolysate of plant containing crocin or derivatives thereof.

The present invention also provides a method to prepare compositions noted herein by hydrolyzing plant materials containing crocin or the derivatives of crocin.

The plant materials containing crocin or derivatives thereof are selected from the group of saffron and gardenia, and includes commercially available saffron.

The hydrolysis of the material can be achieved under acidic or basic conditions. In one aspect, the hydrolysis is conducted under acidic aqueous solutions. Under acidic aqueous conditions, crocin or derivatives thereof, undergo hydrolysis and become or partially become a monoester of crocetin or upon further hydrolysis, produces crocetin.

The monoester of crocetin is shown as below:

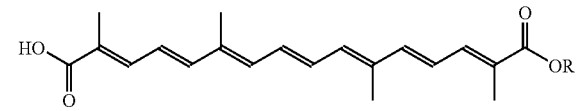

The group "R" denotes gentiobiosyl, glucosyl, or other possible glucosyls.

When R is gentiobiosyl, the monoester of crocetin is crocetin-mono-gentiobioside ester, including trans-type and cis-type isomers.

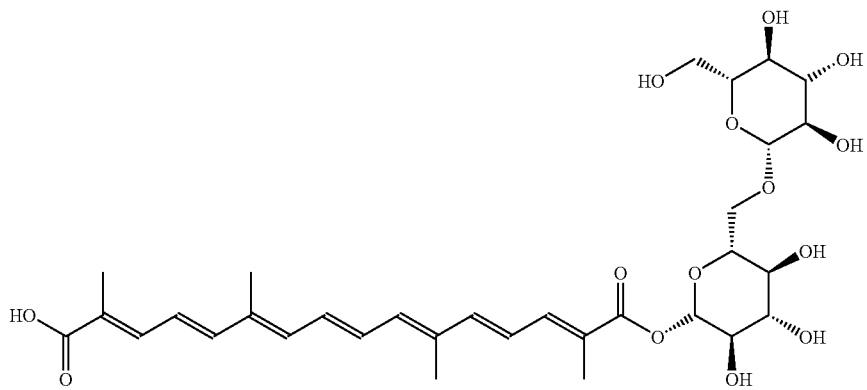

When R is glucosyl, the monoester of crocetin is crocetin-mono-glucoside ester, including trans-type and cis-type isomers.

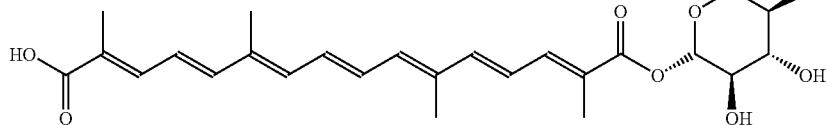

Thus, the present invention provides compositions enriched in a crocetin monoester. The monoester(s) is present in the isolate by more than 1% by weight, more particularly about 10% by weight and even more particularly about 40% by weight.

The hydrosylates of the invention can be further purified by one or more methods known in the art, such as chromatography, gel chromatography, high performance liquid chromatography, crystallization, affinity chromatography, partition chromatography, distillation and the like. Identification of the particular ester (e.g., crocetin monoester) can be accomplished by methods know to those skilled in the art and include $^1$H NMR, chemical degradation, chromatography and spectroscopy, especially homo- and heteronuclear two-dimensional NMR techniques for the characterization of the isolated hydrosylates.

The term "purified" or "isolated" is used in reference to the purification and/or isolation of one or more anthocyanins from an anthocyanin extract as described above. Again using conventional methods known in the art, various components of the anthocyanin extract can be separated into purified materials. In one aspect of the invention, the anthocyanin(s) of the extract are substantially purified and isolated by techniques known in the art. The purity of the purified compounds is generally at least about 90%, preferably at least about 95%, and most preferably at least about 99% and even more preferably at least about 99.9% (e.g. about 100%) by weight.

Owing to various sugar moieties, the above mentioned monoesters of crocetin have various embodiments. Crocetin-mono-gentiobioside ester (trans- or cis-) is a main body of the resulting hydrolysate. This monoester plays the leading role in various uses. At the same time, crocetin-mono-glucoside ester (trans- or cis-) is also useful, although it is not a main ingredient. It is believed, based on the information presented herein, that the monoesters of crocetin provide increased bioavailability of the active component(s) of crocin. This surprising result is noted in the examples below.

By appropriate selection of the hydrolysis conditions, the ratios of crocetin-mono-gentiobioside ester (trans- or cis-) and/or crocetin-mono-glucoside ester (trans- or cis-) can be controlled.

In one embodiment, the final hydrosylate can contain crocetin and/or crocin. During hydrolysis, it is often unavoidable to produce crocetin and/or crocin can remain to a certain extent. Removal of crocetin and/or crocin can be achieved by purification methods noted above if so desired.

It has been found that compositions containing crocin, crocetin and/or crocetin monoester(s) are suitable for use to treat various afflictions described herein. Some of the therapeutic activity of the materials may be related to the high degree of unsaturation found in crocin, crocetin and/or the crocetin monoester(s) where seven conjugated double bonds are present.

In one embodiment, the ratio of crocin:monoester:crocetin is from about (1-25):(1-80):(1-60) on a weigh basis.

In another embodiment, the ratio of crocin:monoester:crocetin is from about (5-15):(10-60):(5-50) on a weight basis.

In still another embodiment, the ratio of crocin:monoester:crocetin is from about (10-15):(30-50):(30-40) on a weight basis.

In still yet another embodiment, the ratio of crocin:monoester:crocetin is from about 10 to about 40 to about 40 on a weight basis.

It should be understood that in the compositions noted herein, the monoester(s) can be crocetin-mono-gentiobioside ester (trans- or cis-) and/or crocetin-mono-glycoside ester (trans- or cis-). In particular, the monoester is crocetin-mono-gentiobioside ester (trans- or cis-).

It has surprisingly been found that that the monoesters of crocetin have good solubility in water. This is advantageous for the delivery and metabolism of the active components.

Furthermore the monoesters have increased bioavailability than crocin or crocetin or mixtures thereof.

Crocetin is insoluble in water. It is soluble in aqueous alkaline solution, which narrows the potential use of crocetin, such as food colorant. Due to poor water-solubility, crocetin is not easily metabolized in vivo.

Crocin has very good water-solubility, and has been referred to as a unique water soluble carotenoid. However, good solubility in an aqueous environment does not provide a physiological advantage to crocin. Due to the molecular weight of the sugar moieties (two gentiobiose groups), crocin has a molecular weight of 976.70 Daltons. As a consequence, it is difficult for such a large molecule to pass through the biomembrane in vivo, which in turn leads to very low bioavailability of crocin.

As active components, crocin and crocetin are both useful for therapeutic treatments, but poor solubility and low bioavailability are two of their drawbacks. Surprisingly, by controlled partial hydrolysis, avoiding full hydrolysis of crocin, the present invention provides a composition with a high content of monoester(s) of crocetin, which provide increased bioavailability in vivo.

Advantageously, crocetin monoesters have only one sugar moiety, which help to maintain water-solubility. For example, one gentiobiose group of crocin is replaced by a carboxyl group, resulting in a change of chemical structure that brings a desirable molecular weight to final product. Therefore, by enhancing water-solubility and lowering molecular weight, the structural disadvantages of crocin/crocetin are circumvented.

The hydrolysate compositions of the invention advantageously provide crocetin monoesters that are useful for therapeutic benefits. On an equivalent weight basis of crocin derived from saffron or gardenia materials, the present invention provides a product with enhanced properties for treatment of depression, cancer prevention, lowering of high cholesterol, treatment of inflammation both therapeutic and preventative, and other potential pharmaceutical and nutraceutical uses as described herein.

The present invention provides that controlled hydrolysis can produce a desired amount of a monoester of crocetin. This can be accomplished by the choice of acid, the concentration of the acid, the temperature range utilized and the length of hydrolysis.

In one aspect, hydrolysis under acidic conditions can be achieved. Suitable acids include, for example, mineral acids, such as hydrochloric acid, phosphoric acid, sulfuric acid, nitric acid, etc. and organic acids, such as oxalic acid, acetic acid, etc.

The hydrolysis reaction temperature can be varied from the room temperature to about 100° C., from about 30 to about 90° C., or from 40-75° C.

Hydrolysis time (reaction time) can be varied according to other reaction conditions. For example heating for a period of from 1 to about 5 hours at a temperature under 70° C., is suitable to achieve hydrolysis to monoester(s).

The hydrolysate compositions of the present invention have increase bioavailability relative to crocin or crocetin. Improved absorption of crocin hydrolysate in vivo enhances the activity of saffron/gardenia plant extract. An equivalent uptake amount of the hydrolysate of the invention produces enhanced effects in contrast to the traditional products of saffron/gardenia. Therefore, the compositions of the present invention are useful in applications of cosmetic, pharmaceutical, nutraceuticals and dietary industries, especially as described below:

Antidepressant

Saffron has been used in folk medicine as antidepressant. Increased absorption of monoester(s) make the product of the present invention valuable for the treatment of depression.

Lowering High Cholesterol

*Biological & Pharmaceutical Bulletin* 28(11) 2106-2110 (2005) disclosed crocin and crocetin derivatives not including monoester(s) significantly decreased triglyceride and total cholesterol. Based on this study, the composition enriched in monoester of crocetin of the present invention will be better at lowering high cholesterol of the body.

Adjusting Bile Secretion:

Bile is a complex fluid containing water, electrolytes and a battery of organic molecules including bile acids, cholesterol, phospholipids and bilirubin that flow through the biliary tract into the small intestine. There are two fundamentally important functions of bile in all species:

1. Bile contains bile acids, which are critical for digestion and absorption of fats and fat-soluble vitamins in the small intestine.
2. Many waste products, including bilirubin, are eliminated from the body by secretion into bile and elimination in feces.

Adult humans produce 400 to 800 ml of bile daily and other animals produce proportionately similar amounts. Secretion into bile is a major route for eliminating cholesterol. Free cholesterol is virtually insoluble in aqueous solutions, but in bile, it is made soluble by bile acids and lipids like lethicin. Gallstones, most of which are composed predominantly of cholesterol, result from processes that allow cholesterol to precipitate from solution in bile.

Bile acids are derivatives of cholesterol synthesized in the hepatocyte. Bile acids contain both hydrophobic (lipid soluble) and polar (hydrophilic) faces. Thus bile acids carry out two important functions; one is emulsification of lipid aggregates; emulsification is not digestion per se, but is of importance because it greatly increases the surface area of fat, making it available for digestion by lipases, which cannot access the inside of lipid droplets. The other is solubilization and transport of lipids in an aqueous environment; bile acids are lipid carriers and are able to solubilize many lipids. Bile acids are also critical for transport and absorption of the fat-soluble vitamins.

Saffron/gardenia extract can adjust bile secretion significantly and is widely used in Asian countries as a Chinese traditional cholagogic drug. Thus the composition enriched in monoester of crocetin of the present invention is effective on ailments caused with digestion disturbances.

Additionally, the hydrolysates of the invention can be used to treat or prevent liver disease. It is believed that by adjusting bile secretion, the hydrolysates of the invention can treat or prevent various liver diseases, including hepatitis, cirrhosis as well as liver cancer, etc.

Gynecological Inflammation:

In Chinese traditional medicine, saffron as a typical herbal medicine is always used for inflammation related to women's gynecological inflammation. Relying on increased bioavailability, the present invention provides a potent therapeutic for gynecological inflammation.

Atherosclerosis:

Atherosclerosis is a slow, progressive disease that causes hardening and narrowing of medium to large blood vessels, such as the aorta and the coronary arteries. Some of the risk factors for atherosclerosis include being overweight or obese, having high cholesterol, high blood pressure, and cigarette smoking. The specific cause of the disease remains unknown. Treatment may involve lifestyle changes, medication, certain medical procedures, or a combination of these. Atherosclerosis prevention starts with recognizing the individual's risk factors for the condition, such as high cholesterol, high blood pressure, or diabetes, and then treating and monitoring these conditions. An important component is adopting a healthy lifestyle, which includes following a healthy diet, maintaining a healthy weight, being physically active, and stopping (or not starting) smoking. In addition, prevention of atherosclerosis may include taking medication. Therefore, based increased bioavailability of the hydrolysates of the invention, cholesterol can be lowered and in turn atherosclerosis can be treated.

Brain Health:

Brain health, also cognitive health, is a growing concern for people of all ages. Parents are learning about the importance of nutrition for their babies, toddlers and adolescents. Teenagers and adults need to be mentally sharp and focused for school and work. Seniors face conditions such as Alzheimer's and cognitive decline as they age. Substances that inhibit AChE activity are candidates for cognitive health. Therefore, with increased AChE inhibition relative to saffron\gardenia compositions, the hydrolysate compositions or monoester(s) of the present invention are useful for brain health brain, as a nutraceutical or drug.

Cardiovascular Diseases:

Cardiovascular disease refers to the class of diseases that involve the heart or blood vessels (arteries and veins), and technically refers to any disease that affects the cardiovascular system. Most countries face high and increasing rates of cardiovascular disease. There is therefore increased emphasis on preventing cardiovascular disease by modifying risk factors, such as healthy eating, exercise and avoidance of smoking. The increased bioavailability of the hydrolysate compositions or monoester(s) of the present invention, relative to traditional saffron/gardenia compositions, help to reduce high cholesterol, which plays an important role in treatment or improvement of cardiovascular diseases.

Age-Related Macular Degeneration Treatment:

The hydrolysates of the invention can be used to treat or prevent age-related macular degeneration (AMD). Age-related macular degeneration (AMD) is a disease associated with aging that gradually destroys sharp, central vision. Central vision is needed for seeing objects clearly and for common daily tasks such as reading and driving. AMD affects the macula, the part of the eye that allows an individual see fine detail. AMD is already a leading cause of vision loss in Americans 60 years and older.

In one aspect, due to the increased bioavailability of the monoesters of the invention (relative to the naturally occurring product(s), the hydrolysates of the present invention provide the ability to treat, prevent or at least reduce the progress of AMD in an individual.

Cancer Treatment:

The hydrolysate compositions or monoesters of the present invention can help reduce or prevent the spread of cancer.

The compositions of the invention can be formulated in a conventional manner using one or more physiologically acceptable carriers, diluents, excipients or auxiliaries that facilitate processing of the compositions into useful preparations.

The compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the hydrolysis compositions in various vehicles. The compositions can also contain formulating agents, such as suspending, stabilizing and/or dispersing agent. The formulations for injection can be presented in unit dosage form, e.g., in ampoules or in multi-dose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the hydrolysate of the present invention can be dried by any art-known technique, such as lyophilization, and reconstituted prior to use.

For transmucosal administration, penetrants appropriate to the barrier to be permeated are used in the formulation. Such penetrants are known in the art.

For oral administration, the compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the crocetin monoester as is well known.

For buccal administration, the compositions can take the form of tablets or lozenges formulated in conventional manner.

For rectal and vaginal routes of administration, the crocetin monoester can be formulated as solutions (for retention enemas) suppositories or ointments containing conventional suppository bases such as cocoa butter or other glycerides.

For nasal administration or administration by inhalation or insufflation, the crocetin monoester of the present invention can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the product of the present invention can be formulated as a depot preparation for administration by implantation or intramuscular injection. The compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the compositions for percutaneous absorption, can be used. To this end, permeation enhancers can be used to facilitate transdermal penetration of the stabilized anthocyanin compositions. Suitable transdermal patches are described in the known arts.

Alternatively, other delivery systems can be employed. Liposomes and emulsions are well-known examples of delivery vehicles that can be used to deliver the composition of the present invention. Certain organic solvents such as dimethylsulfoxide (DMSO) can also be employed, although usually at the cost of greater toxicity.

The compositions can, if desired, be presented in a pack or dispenser device, which can contain one or more unit dosage forms containing the compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight.

The filling of the soft gelatin capsule is liquid (principally a carrier such as rice bran oil or wheat germ oil and/or beeswax if desired) and can include, apart from the compositions, a hydrophilic matrix. The hydrophilic matrix, if present, is a polyethylene glycol having an average molecular weight of from about 200 to 1000. Further ingredients are optionally thickening agents and/or emulsifying agent(s).

The following paragraphs enumerated consecutively from one (1) through 14 provide for various aspects of the present invention. In one embodiment, in a first paragraph (1), the present invention provides a composition, derived from the hydrolysate of a plant containing crocin or derivatives thereof, comprising an increased amount of a crocetin monoester relative to naturally occurring crocetin monoesters found in crocin extracts.

2. A composition according to paragraph 1, wherein the crocetin monoester is crocetin mono glucosyl ester, crocetin mono gentiobiosyl ester or mixtures thereof.

3. A composition according to paragraph 1 or 2, wherein the increased content of crocetin monoester is more than 1% by weight relative to the amount of monoester that occurs naturally.

4. A composition according to paragraph 3, further comprising crocin, crocetin, or other crocetin monoesters.

5. A composition according to paragraph 4, wherein the ratio of crocin:monoester:crocetin is from about (0-25):(1-80):(1-60) by weight.

6. A composition according to paragraph 5, wherein the ratio of crocin:monoester:crocetin is from about (5-15):(10-60):(5-50) by weight.

7. A composition according to paragraph 6, wherein the ratio of crocin:monoester:crocetin is from about (10-15):(30-50):(30-40) by weight.

8. A composition according to paragraph 6, wherein the ratio of crocin:monoester:crocetin is from about 10 to about 40 to about 40 by weight.

9. A composition according to any of the preceding paragraphs, wherein the plant containing crocin is gardenia or saffron.

10. A method to prepare a composition according to paragraph 5, wherein the hydrolysate is from the hydrolysis under acidic or basic conditions.

11. A method according to paragraph 10, wherein the acidic hydrolysis uses HCl, phosphoric acid or oxalic acid.

12. A use of the composition according to any of the paragraphs 1-9 in the comestic, pharmaceutical, nutraceutical or dietary.

13. A use of the composition according to any of the paragraphs 1-9 in treating, preventing or improving depression, cancer, gynecological inflammation, atherosclerosis, cardiovascular diseases, Alzheimer's disease, aged-related macular degeneration, hepatitis, cirrhosis, liver cancer lowering high cholesterol, adjusting bile secretion, or enhancing brain health.

14. The composition, method or use of any of paragraphs 1 through 13, wherein the hydrolysate has been isolated and/or purified.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLE 1

10 g gardenia yellow was dissolved in 20 g water and 8 g hydrochloric acid (35% by volume). The mixture was heated to 50° C. and reacted for 2.5 h with agitation under a nitrogen atmosphere. A dark red solid was washed by 200 mL water and then was dissolved in 200 mL methanol. The solution was filtered and the methanol was distilled to afford 3.1 g of a dark red solid.

HPLC Determination

HPLC analysis was performed with a Agilent1100 system equipped with a C-18 chromatographic column (75 mm×4.6 mm). AUV-Vis detector monitored the elution profile at 440 nm wavelength. The mobile phase was a solution consisting of 80% methanol and 20% water which contained 0.2% acetic acid.

The components of the red solid are specified in Table 1 below and in FIG. 1:

TABLE 1

| Peak content | Time | Area | Height | Width | Area % | Symmetry |
| --- | --- | --- | --- | --- | --- | --- |
| Crocin | 1.444 | 967.6 | 83.9 | 0.152 | 7.386 | 1.092 |
| monoester of crocetin | 1.866 | 4348.7 | 544.2 | 0.1165 | 33.192 | 0.599 |
| Crocetin | 4.783 | 2505.8 | 220.3 | 0.1691 | 19.125 | 0.655 |
| others | 8.323 | 1535.3 | 99.4 | 0.2355 | 11.718 | 0.854 |

EXAMPLE 2

Monoester of Crocetin Preparation (Test SN: C-0118PA)

600 g gardenia yellow (commercial product, UV %=20%, 422 nm) was mixed with 1800 g phosphoric acid and 1200 g water. The mixture was stirred at 75° C. for two hours. The resulting material was washed with 1200 mL water. After water washing, the end product weighed 600 g, and was a dark red solid. FIG. 1 and Table 2 provide components and relative amounts of components.

HPLC Analytical Method:
Instrument: Waters HPLC
Column: RP18, 3.9 mm×150 mm×5 μm
Mobile phase: methanol/water=80/20
Flow rate: 0.5 mL/min
Detection: 440 nm

TABLE 2

| Peak No. | Peak content | RT | Area | % Area | Height |
|---|---|---|---|---|---|
| 1 | Crocin | 2.457 | 2652457 | 12.33 | 71659 |
| 2 | Monoester of crocetin | 4.449 | 9385695 | 43.63 | 290442 |
| 3 | other component | 7.600 | 283910 | 1.32 | 3921 |
| 4 | other component | 8.867 | 29041 | 0.14 | 1867 |
| 5 | Crocetin 1* | 16.036 | 7741568 | 35.99 | 183094 |
| 6 | Crocetin 2* | 17.901 | 1418810 | 6.60 | 30594 |

*Isomeric compound

The percentage of peaks are noted below:
Crocin: 12.33%
Monoester: 43.63%
Crocetin: 41.59%

EXAMPLE 3

Monoester of Crocetin Preparation (Test SN: C-0117)

Figure 3:
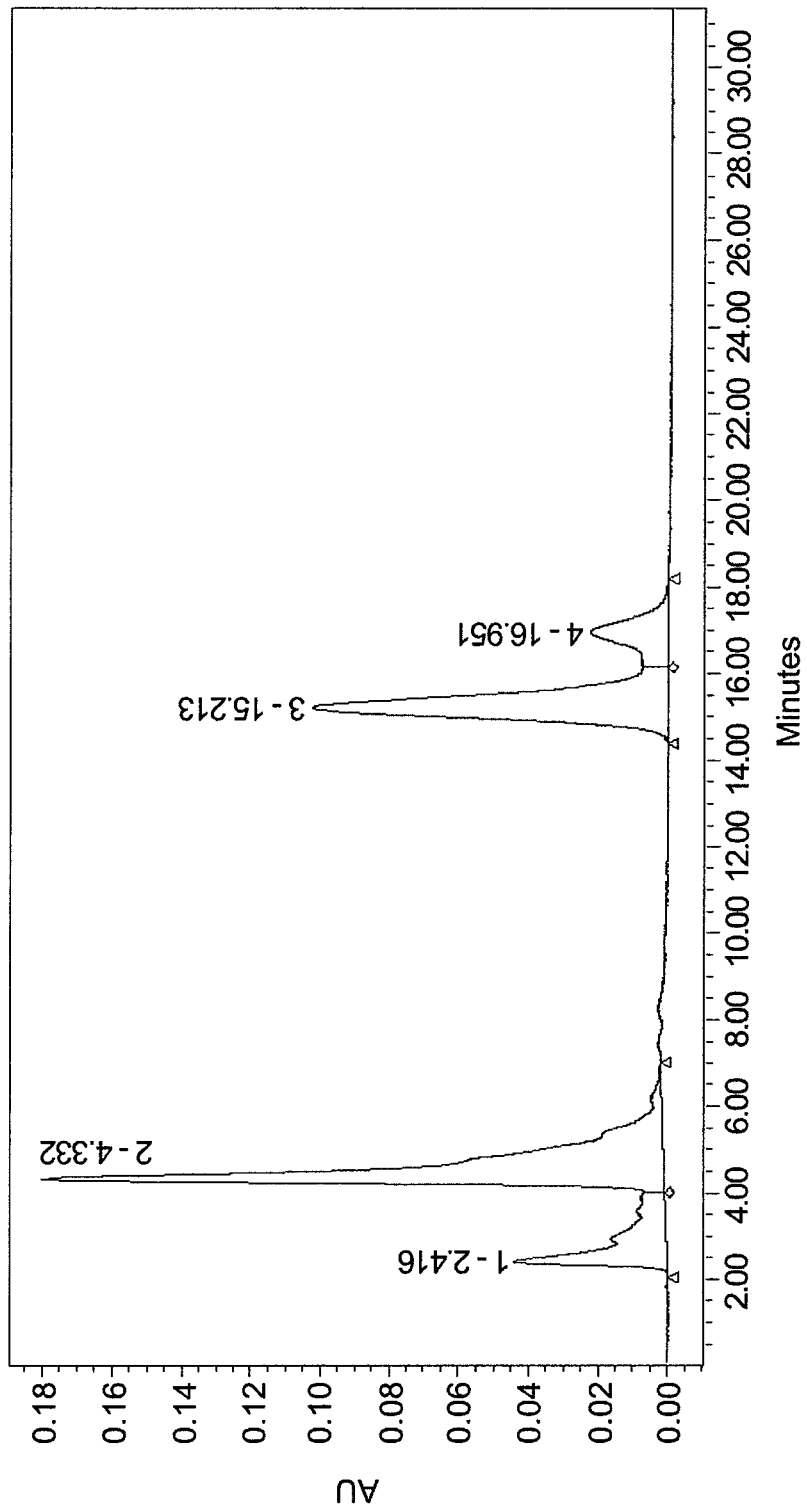
FIG. 3 is an HPLC chromatogram of a hydrolysate of another embodiment of the invention.

1 g gardenia yellow (commercial product, UV %=20%, 422 nm) was mixed with 20 g phosphoric acid aqueous solution (5% by weight). The mixture was stirred at 50° C. for 40 min, and then 4 g concentrated HCl and 1 g water were added to the reaction system drop by drop until complete. After vacuum filtration, the resulting material was resolved in ethanol to form a saturated solution. Water was added dropwise until precipitation occurred. The upper clear liquid was analyzed by HPLC. Analytical analysis was performed as in example 2. The results are provides in FIG. 3 and Table 3 as shown below:

TABLE 3

| Peak No. | Peak content | RT | Area | % Area | Height |
|---|---|---|---|---|---|
| 1 | Crocin | 2.416 | 1567184 | 13.11 | 43748 |
| 2 | Monoester of crocetin | 4.332 | 5402877 | 45.20 | 179077 |
| 3 | Crocetin 1* | 15.213 | 3932041 | 32.89 | 102103 |
| 4 | Crocetin 2* | 16.951 | 1051476 | 8.80 | 21909 |

*isomeric compound

Percentage of peaks are noted as:
Crocin: 13.11%
Monoester: 45.20%
Crocetin: 41.69%.

EXAMPLE 4

Monoester of Crocetin Preparation (Test SN: C-1030)

Figure 4:
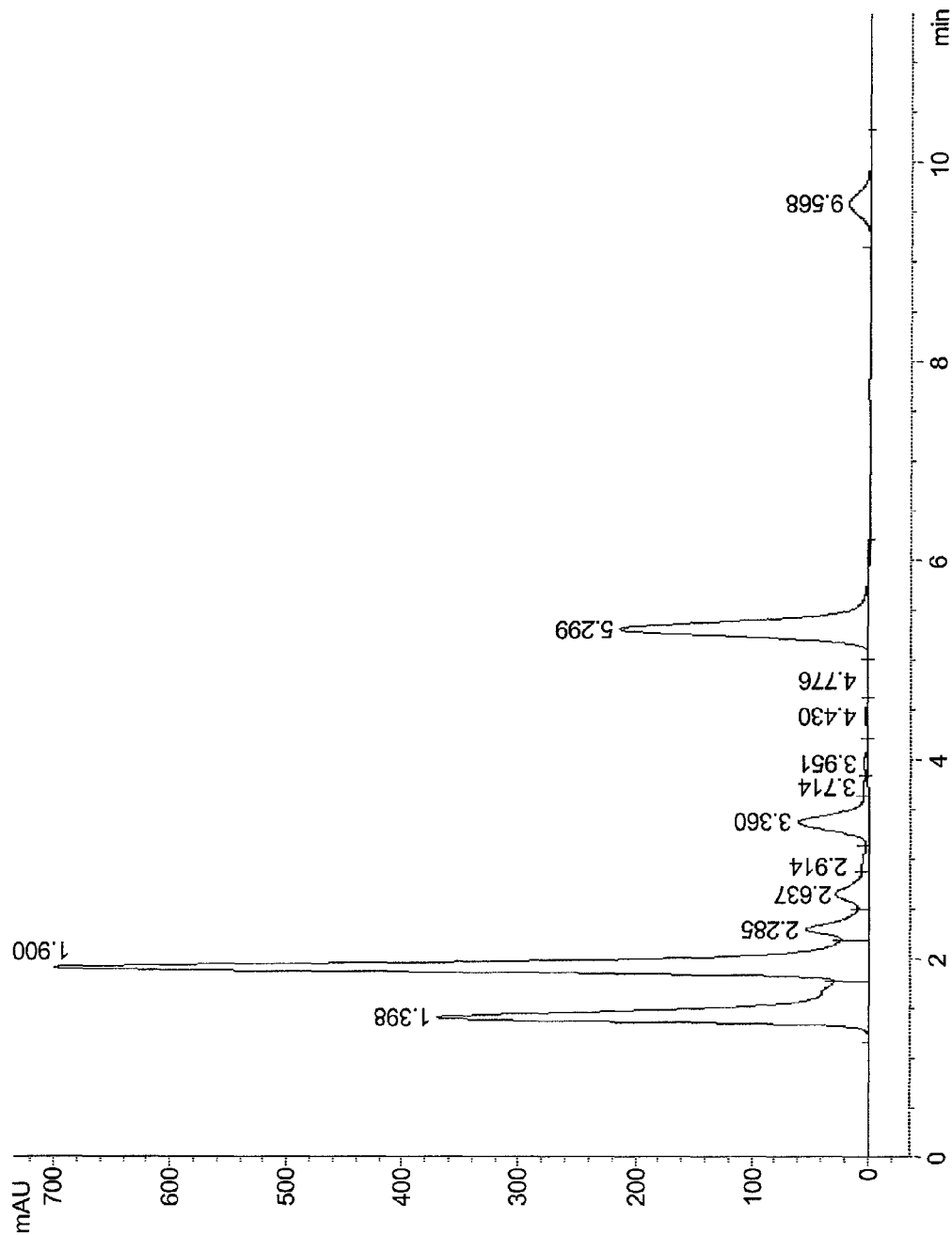
FIG. 4 is an HPLC chromatogram of a hydrolysate of another embodiment of the invention.

5 g gardenia yellow (commercial product, UV %=20%, 422 nm) was mixed with 15 g HCl aqueous solution (concentrated HCl; 33% by weight). The mixture was heated from 4° C. to 50° C. within 10 min, and then maintained at 50° C. for 30 min with stirring. HPLC analysis results are provided in FIG. 4 and Table 4 below:

Crocin is 25.76%, monoester of crocetin is 39.76% and crocetin is 17.51%.

TABLE 4

| Peak No. | Peak content | RT/min. | Area/mAU | Height | Area/% |
|---|---|---|---|---|---|
| 1 | Crocin | 1.398 | 3474.07642 | 370.17142 | 25.7611 |
| 2 | Monoester of crocetin | 1.900 | 5362.00537 | 702.10504 | 39.7605 |
| 3 | \ | 2.285 | 559.32758 | 54.73783 | 4.1475 |
| 4 | \ | 2.637 | 368.39673 | 29.34089 | 2.7317 |
| 5 | \ | 2.914 | 76.27254 | 6.23904 | 0.5656 |
| 6 | \ | 3.360 | 732.10663 | 61.28264 | 5.4287 |
| 7 | \ | 3.714 | 57.55760 | 5.38762 | 0.4268 |
| 8 | \ | 3.951 | 73.40577 | 5.64571 | 0.5443 |
| 9 | \ | 4.430 | 57.58480 | 3.71721 | 0.4270 |
| 10 | \ | 4.776 | 37.58595 | 2.23643 | 0.2787 |
| 11 | Crocetin | 5.299 | 2361.50269 | 215.51270 | 17.5111 |
| 12 | \ | 9.568 | 325.93753 | 18.75234 | 2.4169 |

Figure 5:
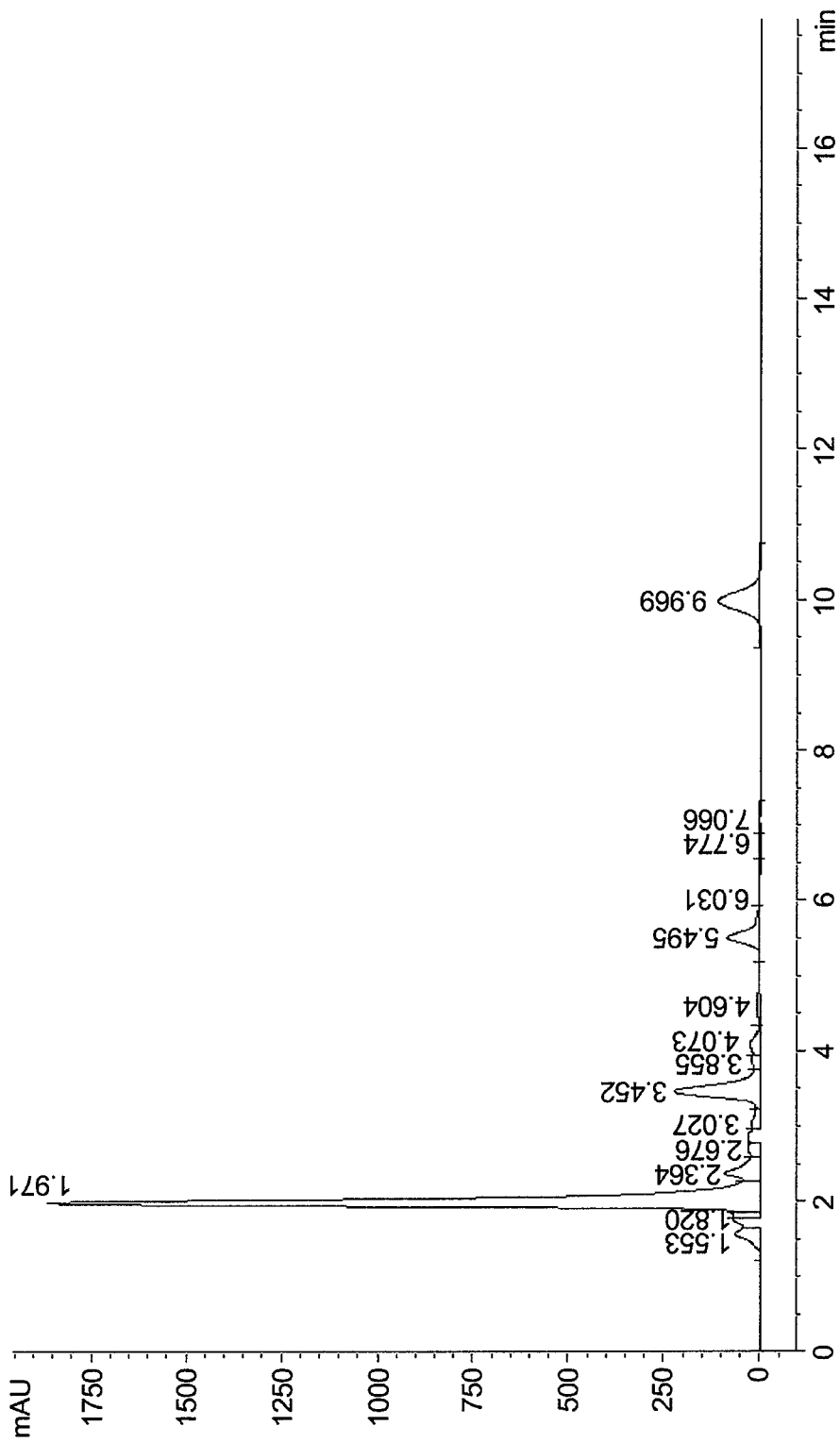
FIG. 5 is an HPLC chromatogram of a hydrolysate of another embodiment of the invention.

After filtration, solid was collected and added to methanol to form a saturated solution. An equivalent volume of water was added to the solution and filtered. The upper clear liquid was analyzed by HPLC. Analysis condition were the same as example 1 and the results are shown in Table 5 and FIG. 5.

TABLE 5

| Peak No. | Peak content | RT/min | Area/mAU | Height | Area/% |
|---|---|---|---|---|---|
| 1 | \ | 1.554 | 706.77954 | 66.80975 | 2.9696 |
| 2 | \ | 1.820 | 327.97046 | 74.31164 | 1.3780 |
| 3 | Monoester of crocetin | 1.972 | 1.40835e4 | 1863.98206 | 59.1736 |
| 4 | \ | 2.364 | 1042.99097 | 94.24978 | 4.3823 |
| 5 | \ | 2.676 | 318.79172 | 32.89029 | 1.3394 |
| 6 | \ | 3.027 | 266.48245 | 22.55992 | 1.1197 |
| 7 | \ | 3.453 | 2769.08813 | 224.98495 | 11.6347 |
| 8 | \ | 3.855 | 235.35849 | 24.58457 | 0.9889 |
| 9 | \ | 4.07 | 401.77420 | 26.55097 | 1.6881 |
| 10 | \ | 4.604 | 315.48105 | 11.24618 | 1.3255 |
| 11 | Crocetin | 5.495 | 1130.45105 | 87.56268 | 4.7497 |
| 12 | \ | 6.031 | 134.95776 | 6.12393 | 0.5670 |
| 13 | \ | 6.774 | 35.64629 | 2.08088 | 0.1498 |
| 14 | \ | 7.476 | 34.00674 | 1.84287 | 0.1429 |
| 15 | \ | 9.969 | 1997.00537 | 111.09497 | 8.3907 |

Crocin: 0
Monoester: 59.17%
Crocetin: 4.75%

The example provides an increased content of crocetin monoester after hydrolysis and purification.

EXAMPLE 5

This example focuses on an inhibition of Acetycholinesterase (AChE) by Crocin, monoester of crocetin and Crocetin.

Cholinesterase Assays:

Inhibitor solution: 10 mg of the corresponding samples were respectively dissolved in 1 ml methanol.

Chromogen solution: 0.1 M Sodium phosphate buffer (pH=8, NaOH) was mixed with solution A at a ratio of 30:1.

Solution A: 39.6 mg 5,5'-dithio-bis[2-nitrobenzoic acid] and 15.0 mg $NaHCO_3$ were weighed into a 10 ml flask and filled to the mark with 0.1 M Sodium-phosphate buffer (pH=7, NaOH).

Enzyme solution: A solution of human acetylcholinesterase containing 70 IU enzyme activity/ml $H_2O$ was prepared.

Substrate solution: 115.7 mg acetylthiocholine-iodide was weighed into a 10 ml flask and filled to the mark with $H_2O$.

10 µl inhibitor solution was mixed with 185 µl chromogen solution and 10 µl enzyme solution. The solution was incubated for 10 minutes at room temperature with shaking. 5 W substrate solution was added and the increase in absorption at 412 nm was recorded until no more increase was observed (3-5 minutes). The results are noted in Table 6.

TABLE 6

| Sample | mg/ml | AChE activity % | Inhibition of AChE activity % |
|---|---|---|---|
| Neg Control | / | 100.0 | 0.0 |
| Galanthamin•HBr * | 0.50 | 2.6 | 97.4 |
| Monoester * | 0.50 | 10.8 | 89.2 |
| Crocin | 0.50 | 52.7 | 47.3 |
| Crocetin | 0.50 | 92.5 | 7.5 |

* Galanthamin•HBr is product No. G1660 in Sigma product directory, a cholinesterase inhibitor.
* Monoester is monoester of crocetin from example 1.

Figure 6:
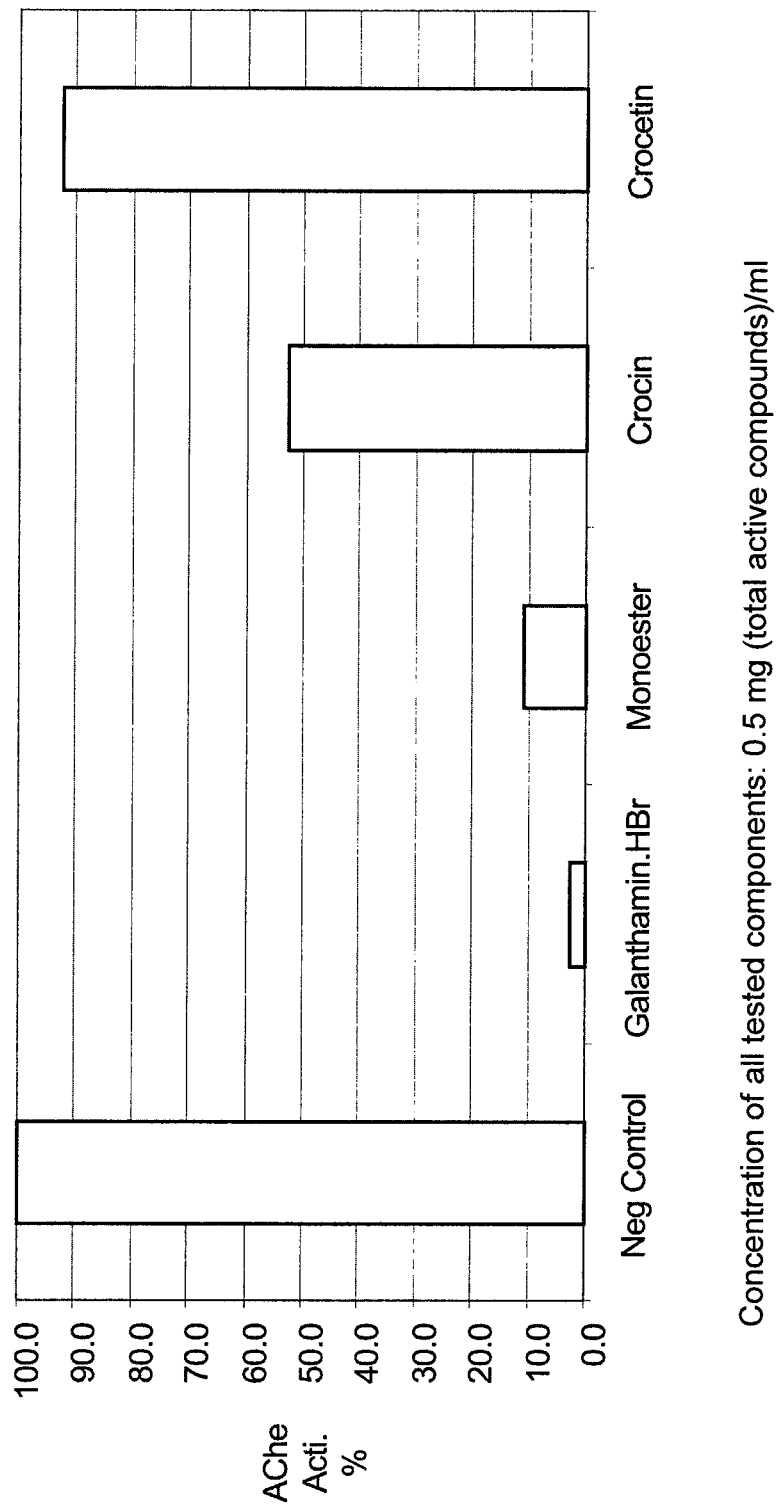
FIG. 6 is a graphical representation of AChE inhibition by hydrolysates of the invention.

FIG. 6 demonstrates inhibition of AChE activity by various samples.

EXAMPLE 6

Cellular Uptake of Crocin and Crocetin in CaCo-2 Cells

CaCo-2 cells were incubated with 10 mg Gardenia extract and 10 mg crocetin/100 mL medium. The test compounds were dissolved in methanol and then diluted with incubation medium. Incubations were performed at 37° C. for 30, 60 and 120 minutes. At each time point, 3 wells were processed for analysis by collection of the incubation medium and extraction of crocin related esters or crocetin absorbed into the cells.

The content of crocetin related esters and crocetin in the sample used for incubation testing was determined. Table 7 is a summary of analytical results.

Table 7 provides the content of test solution prior to incubation:

|  | mg/100 ml | Area-% Fingerprint* | |
|---|---|---|---|
| Crocetin | 9.82 | not applicable | |
| Crocetin-related compounds in Gardenia sample extract (UV/VIS spectroscopy) | 5.22 | DGTC | 45.3 |
|  |  | NGTC | 18.1 |
|  |  | DGCC | 16.6 |
|  |  | GTC | 9.7 |

*Abbreviations:
DGTC digentobiosyl-(trans)crocetin;
NGTC neapolitanosyl-glucosyl-(trans)crocetin;
DGCC digentobiosyl-(cis)crocetin;
GTC gentobiosyl-(trans)crocetin Table 8 provides the corresponding data for the test solution obtained after 120 minutes.

|  | mg/100 ml | Area-% Fingerprint* | |
|---|---|---|---|
| Crocetin | 9.77 | not applicable | |
| Crocetin-related compounds in Gardenia sample extract (UV/VIS spectroscopy) | 5.29 | DGTC | 43.4 |
|  |  | NGTC | 17.9 |
|  |  | DGCC | 15.2 |
|  |  | GTC | 10.3 |

This comparison indicates that the compounds tested are stable under test assay conditions and that the content after 120 minutes of incubation is not different from the sample analyzed prior to incubation.

Table 9 is a summary for the analysis of the cellular content, indicative for the portion absorbed is shown.

Table 9 shows tabulated concentrations of crocetin and crocetin-related compounds in the cells:

| Time (min) | Crocetin (HPLC)* | UV/VIS extinction | HPLC peaks** |
|---|---|---|---|
| 0 | BLD | <0.03 | not detected |
| 30 | BLD | <0.03 | not detected |
| 60 | BLD | <0.03 | not detected |
| 120 | BLD | <0.03 | not detected |

*BLD = <0.01 mg/100 ml
**for DGTC, NGTC, DGCC and GTC

EXAMPLE 7

Extension of Trial Introducing Gardenia-Extract of the Present Invention

Methods applied were similar to example 6, except that gardenia hydrolysate was introduced into the experiments and that the concentration of the samples was doubled to 20 mg/100 ml.

The tests were performed in replicate and the results are expressed as %-uptake based on peak areas measured by HPLC/UV.

Table 10 shows the test results obtained:

| Sample | Gardenia extract | Gardenia hydrolysate of example 1 | Pure crocetin compound |
|---|---|---|---|
| % overall uptake of crocin related compounds | 0.48 | 0.76 | 0.53 |
| % uptake of crocetin* | 0.44 | 0.47 | 0.53 |
| % uptake of crocetin-diesters* | 0.01 | 0.01 | — |
| % uptake of crocetin-monoesters* | 0.02 | 0.28 | — |

*proportion on overall absorption

As seen above, the overall absorption of gardenia hydrolysate of example 1 is higher than gardenia extract or pure crocetin. The results indicate that monoesters are more bio-available than diesters of crocetin.

Methods

Culturing of CaCo-2 Cells

CaCo-2 cells were cultured in Dulbeccos's Modified Eagle Medium containing 20% fetal bovine serum, 1.2% nonessential amino acids, 0.83 mM L-glutamine, 1.2% penicillinstreptomycin and 0.1% mercaptoethanole in an atmosphere of 5% $CO_2$ and 95% air at 37° C.

Cells were grown in 75 cm² culture-flasks (T75) and subcultured after one week (every other day washed with PBS buffer, removed with trypsin and transferred to a new culture flask).

CaCo-2 Test

For experiments, cells were seeded in 6 well plates at a density of 3*10⁵ cells per well and grown in an atmosphere of 5% $CO_2$ and 95% air at 37° C., 7 to 8 days until confluence was reached. The cells were washed with PBS buffer, incubated with 4 ml medium containing the suspended samples for 30, 60 or 120 minutes.

After the corresponding incubation time, the cells were washed with PBS buffer/MeOH=70/30 and removed using 1 ml of MeOH. Cells were sonicated 3 times for 30 seconds, centrifuged for 10 min and the pellets were discarded. The supernatant was used as sample for HPLC and UV/VIS-analysis.

| Analysis of Crocetin and crocetin-related esters | |
| --- | --- |
| Pump: | Merck Quaternary Gradient pump 6200, Merck AS 2000, HP-MVD 1050, column oven Tech Lab |
| Column: | Waters Sperisorb OD2, 250 × 4.6 mm |
| Mobile phase: | (a) MeOH with 0.1% formic acid |
| | (b) 0.1% formic acid |
| Gradient: | 30% (a) for 5 minutes, increase to 60% (b) in 20 minutes |
| Flow Rate: | 1 mL/min |
| Temperature: | Ambient |
| Injection volume: | 20 µl |
| Detection: | 423 nm |

Standard Preparation (Crocetin)

An appropriate amount of standard was transferred into a 10 mL flask and dissolved in 3 mL methanol and filled to the mark with water. Dilutions were prepared in mobile phase.

Data Evaluation

Quantification was performed by external standardization after linear regression analysis.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A pharmaceutical or nutraceuctical composition, derived from the extract of a plant containing crocin, comprising a hydrolysate of the extract enriched for the amount of a crocetin monoester of glucosyl and/or gentiobisyl 1% or greater relative to the non-hydrolysate wherein the monoester is derived from crocin during hydrolysis.

2. A pharmaceutical or nutraceuctical composition according to claim 1, further comprising crocin and/or crocetin.

3. A pharmaceutical or nutraceuctical composition according to claim 2, wherein the ratio of crocin: monoester : crocetin is from about (0-25):(1-80):(1-60) by weight.

4. A pharmaceutical or nutraceuctical composition according to claim 3, wherein the ratio of crocin : monoester : crocetin is from about (5-15):(10-60):(5-50) by weight.

5. A pharmaceutical or nutraceuctical composition according to claim 4, wherein the ratio of crocin:monoester:crocetin is from about (10-15):(30-50):(30-40) by weight.

6. A pharmaceutical or nutraceuctical composition according to claim 4, wherein the ratio of crocin:monoester:crocetin is from about 10 to about 40 to about 40 by weight.

7. A pharmaceutical or nutraceuctical composition according to claim 1, wherein the plant containing crocin is gardenia or saffron.

8. A method to prepare a composition according to claim 1, comprising:
obtaining a crocin extract low in crocetin monoesters;
hydrolyzing the crocin extract to provide a hydrolysate containing crocetin monoesters;
preparing a pharmaceutical or nutraceuctical composition from the hydrolysate
wherein the crocetin monoesters are derived from crocin hydrolysis wherein the hydrolysate is from the hydrolysis under acidic or basic conditions.

9. A method according to claim 8, wherein the acidic hydrolysis uses HC1, phosphoric acid or oxalic acid.

10. A cosmetic, pharmaceutical, nutraceutical or dietary supplement comprising the composition of claim 1 and a carrier.

11. A method to treat or improve, depression, cancer, gynecological inflammation, atherosclerosis, cardiovascular diseases, Alzheimer's disease, aged-related macular degeneration, hepatitis, cirrhosis, lowering high cholesterol, adjusting bile secretion, or enhancing brain health comprising the step of administering to an individual in need thereof an effective amount of a composition of claim 1 and, optionally, a carrier, whereby depression, cancer, gynecological inflammation, atherosclerosis, cardiovascular diseases, Alzheimer's disease, aged-related macular degeneration, hepatitis, cirrhosis, lowering high cholesterol, adjusting bile secretion, or enhancing brain health is treated, or improved.

12. The pharmaceutical or nutraceuctical composition according to claim 1, wherein the hydrolysate has been isolated and/or purified.

13. The supplement of claim 10, wherein the hydrolysate has been isolated and/or purified.

14. The method of claim 11, wherein the hydrolysate has been isolated and/or purified.

* * * * *